(12) United States Patent
Szymkowiak et al.

(10) Patent No.: US 9,945,833 B2
(45) Date of Patent: Apr. 17, 2018

(54) FACILITY FOR PROCESSING A MULTIPHASE FLUID AND METHOD FOR CHARACTERIZING SAID FLUID ONLINE

(71) Applicant: WINTECH GLOBAL, Lyons (FR)

(72) Inventors: Bertrand Jean Szymkowiak, Lyons (FR); Yves Louis Léon Marie Lecoffre, Grenoble (FR); Guillaume Daniel Ghislain Maj, St. Martin d'heres (FR)

(73) Assignee: WINTECH GLOBAL, Lyons (FR)

( * ) Notice: Subject to any disclaimer, the term of this patent is extended or adjusted under 35 U.S.C. 154(b) by 132 days.

(21) Appl. No.: 14/427,823

(22) PCT Filed: Sep. 18, 2013

(86) PCT No.: PCT/FR2013/052158
§ 371 (c)(1),
(2) Date: Mar. 12, 2015

(87) PCT Pub. No.: WO2014/044973
PCT Pub. Date: Mar. 27, 2014

(65) Prior Publication Data
US 2015/0247836 A1 Sep. 3, 2015

(30) Foreign Application Priority Data

Sep. 18, 2012 (FR) .................................... 12 58761

(51) Int. Cl.
*G01N 33/28* (2006.01)
*G01F 3/00* (2006.01)
(Continued)

(52) U.S. Cl.
CPC ..... *G01N 33/2841* (2013.01); *B01D 17/0208* (2013.01); *B01D 17/0211* (2013.01);
(Continued)

(58) Field of Classification Search
CPC .............. G01N 33/18; G01N 33/2841; G01N 2001/4083; G01F 3/00
See application file for complete search history.

(56) References Cited

U.S. PATENT DOCUMENTS

| 5,526,684 A | 6/1996 | Liu et al. |
| 2005/0016292 A1 | 1/2005 | Dutton et al. |

(Continued)

FOREIGN PATENT DOCUMENTS

| DE | 102005017614 | 10/2006 |
| WO | WO2006085772 | 8/2006 |

OTHER PUBLICATIONS

International Search Report for PCT Application PCT/FR2013/052158, EPO, dated Jan. 22, 2014.

*Primary Examiner* — Daniel S Larkin (57) ABSTRACT

A plant (1) for the treatment of a multiphasic fluid and method for line-characterization of the fluid wherein the plant (1) comprises a circuit (4) within which the fluid is intended to circulate and being characterized in that it comprises a characterization tool (3) comprising at least an analysis settler (6) adapted to separate the phases to obtain so-called separated phases and a means (9) for combining the separated phases. The plant (1) is designed so that a fraction of the fluid circulating within the circuit (4) circulates within the tool (3) to pass through the analysis settler (6) so that the phases of the fluid are separated then discharged into the circuit (4). The combining means (9) is designed so as to combine the separated phases.

9 Claims, 2 Drawing Sheets

(51) Int. Cl.
 *G01N 33/18* (2006.01)
 *B01D 17/02* (2006.01)
 *E21B 43/34* (2006.01)
 *G01N 1/40* (2006.01)

(52) U.S. Cl.
 CPC .......... *B01D 17/0214* (2013.01); *E21B 43/34* (2013.01); *G01F 3/00* (2013.01); *G01N 33/18* (2013.01); *G01N 2001/4083* (2013.01)

(56) References Cited

U.S. PATENT DOCUMENTS

2007/0274842 A1 11/2007 Campen et al.
2010/0174517 A1 7/2010 Slupphaug et al.

FIG.1

FACILITY FOR PROCESSING A MULTIPHASE FLUID AND METHOD FOR CHARACTERIZING SAID FLUID ONLINE

TECHNICAL FIELD

The present invention relates to the general technical field of multiphasic fluid treatment, and relates more particularly to a plant intended to be used in an industrial framework, for example in the petroleum production, wastewater treatment, food-processing, cosmetic or pharmaceutic sectors.

The present invention more particularly relates to a plant for the treatment of a multiphasic fluid comprising at least two phases of different respective densities, said plant comprising a circuit within which said fluid is intended to circulate.

The present invention also relates to a method for characterizing a multiphasic fluid comprising at least two phases of different respective densities, said fluid being intended to circulate within a circuit.

PRIOR ART

The multiphasic fluids are formed of phases of different respective densities. Working with such fluids is current in many industries. A phase can be gaseous, liquid or solid. Within the meaning of the invention, a liquid constitutes a phase when the different elements that compose it cannot be separated by gravity. Hence, a mixture of miscible liquids constitutes a single and same phase.

In some industrial processes, it proves necessary to separate the different phases of a same fluid, i.e. to separate one or several components within a same composition. It is in particular the case in the sites of production or treatment of petroleum fluids, which have in particular for object to separate the water and the crude petroleum present in the fluid collected at the outlet of the well connected to the petroleum deposit.

In other situations, it is simply useful to know the characteristics of the separation of the different phases of the multiphasic fluid under the effect of gravity. These characteristics may prove useful to pilot optimally the industrial plant within which the fluid circulates. By way of example, it may be aimed to be sure that the different phases of a fluid have not the time to be separated during an industrial process including in particular a phase of storage, or more generally a phase of transfer, for example by flowing in a duct connecting two successive steps of an industrial process.

By way of illustrative and non-limitative example, the focus will be placed on the case where the treatment plant constitutes one element of a petroleum production unit, said fluid comprising petroleum. This example constitutes the preferential application of the invention. An aqueous contamination of petroleum may occur when the deposit is in contact with a phreatic groundwater. From then on, an emulsion is formed, including in particular an aqueous phase and an organic phase, droplets of one of the phases being present in the other phase. This emulsion issued from petroleum extraction further generally comprises a gaseous phase. Before any subsequent operation, it is hence necessary to separate the different phases to collect the crude petroleum (the liquid organic phase) and to discharge the aqueous phase on the one hand and the gaseous phase on the other hand. It is essential that this separation is particularly efficient because regulations, intended to protect the environment, force the petroleum producers to limit the petroleum slops and hence to strongly reduce the content of the organic phase within the aqueous phase intended to be discharged in the natural environment. The separation plant must hence fulfil requirements liable to be severe as regard the quality of the exiting fluids.

This separation is conventionally performed by means of gravity settlers, also called separator tanks. They are implemented to separate the crude petroleum and the aqueous phase and are generally in the form of tanks of high inner volume within which circulates continuously the multiphasic fluid the phases of which are desired to be separated. The time of residence of the multiphase fluid (emulsion) within the settler has to be long enough to allow the phases of different densities to be separated by gravity. This time hence constitutes an important parameter in the operation of the settler. A conventional example of a settler is that formed of a main chamber divided into two sub-chambers separated by a wall open in the upper part for the two sub-chambers to communicate with each other. The emulsion is introduced into the first sub-chamber and only one of the two phases is supposed to go to the second sub-chamber. The two hence-separated phases are then continuously discharged from the settler through corresponding outlets formed in the first and in the second sub-chambers, respectively. Within the meaning of the invention, a separated phase may all the same contain residual quantities of another phase of said fluid. Of course, other types of settlers exist and the invention is not limited to a particular type of settler.

The petroleum settlers generally operate under high pressure and high temperature. Conventionally, the settlers used are adapted to impart a time of residence of about ten minutes therein, at a flow rate of the order of 750 m$^3$/h, for example, so that the volume of the main chamber of the settler is generally of the order of 120 m$^3$.

Moreover, the physico-chemical properties of the emulsion and the flow rate to be treated determine the design of the petroleum settler, in particular as regards the volume of the first sub-chamber. The petroleum settlers are hence generally designed for a given site of production after a preliminary analysis of the first quantities of emulsion extracted from the petroleum well, the more often at the end of the phase of exploration of the petroleum deposit. The settlers are hence designed during a design phase so as to separate a certain type of emulsion whose proportions of organic and aqueous phases are known.

Now, the petroleum emulsion entering into the settler has no constant physico-chemical properties over time and these properties can even strongly vary. In particular, the collected crude can be of different composition according to the various pockets exploited in the deposit or according to the different chemical additives it has been necessary to inject into the well to allow a better recovery of this petroleum. Moreover, the deposits generally produce an emulsion predominantly composed of oil at the beginning of the production and predominantly consisted of water at end of life.

Hence, the settler can generally not operate optimally at a constant flow rate in a site of petroleum production, because the emulsion entering into the settler can itself vary during the exploitation. It is hence necessary to know the evolution of the characteristics of separation of the entering emulsion over time to be able to pilot the operation of the settler. By knowing perfectly the properties of the entering emulsion, it is from then on possible either to adjust the flow rate of the entering emulsion flow, so as to modify the time of residence, or to introduce into the settler or upstream thereof (according to the flowing direction of the fluid) chemical additives (of the demulsifier type) supposed to accelerate the separation of the different phases. These two actions, possibly complementary to each other, must allow to achieve the aimed objects as regards the quality of the fluids at the outlet of the separator. Piloting the settler by acting on these two parameters is particularly expensive (reducing the flow rate means reducing the production and the selling of petroleum whereas the addition of chemical additives entails a non-negligible cost and delicate settings) and it is hence essential that the measures indicating the effect of the variation of either one of these parameters on the quality of the fluids at the outlet of the separator are reliable.

However, the piloting of the settler proves particularly complex to implement because there exists today no reliable method that allows a very good characterization of the emulsion.

One of the methods used consists in performing different physico-chemical analyses of the entering emulsion. These analyses are performed on a sample taken punctually upstream of the settler. The taken sample is then generally sent to a laboratory in which are performed, in particular, measurements of density, viscosity or contents of water in oil or oil in water. These analyses of the entering emulsion are generally supplemented with measurements performed on the separated phases at the outlet of the settler. For that purpose, a sample is taken at the different outlets of the settler and said samples are sent to a laboratory. Based on the analysis of all the results relating to the entering emulsion and the exiting separated phases, adjustments are proposed regarding the operating conditions (flow rate or addition of additives) to improve the operation of the settler.

But such a method proves not to be optimal for the following reasons.

Firstly, there is necessary a non-negligible time lapse between the sample-taking and the results of the measurement, time lapse during which the emulsion treated by the settler is liable to vary and during which the physico-chemical properties of the sample taken may vary, hence making certain measurements performed null and void, or at least difficult to exploit. This of course constitutes an important failure of such a method of adjustment due to the failure of reactivity that ensures therefrom. In particular, during the transportation, pressures and temperatures vary and the separation of phases is performed in a particular manner, different from the emulsion behaviour within the industrial plant.

Moreover, these analyses simply allow to measure certain properties of the emulsion and do not give a measurement of the emulsion behaviour when the latter circulates within the plant. Besides, these measurements cannot in any way anticipate a future dysfunction of the settler and are in reality only rough indicators for piloting the operation of the plant.

Besides, the so-performed measurements do not allow to characterize independently the different physical phenomena occurring during the process of phase separation under the effect of gravity. Indeed, the separation is firstly conditioned by the settlement that is the propensity of the droplets of one phase in another one to be separated under the effect of gravity; secondly, the separation depends on the coalescence that is the phenomenon by which two drops of a same phase are combined into a single one. The analyses performed on taken samples do not allow to discriminate these two phenomena (settlement or coalescence), which would yet constitute precious information for characterizing the multiphasic fluid and hence correctly piloting the plant within which it circulates.

Moreover, this method being based on measurements made on samples do not either allow to easily and reliably be sure of the quality of the solutions implemented (additions of additives or variation of the flow rate).

It is also to be noted that similar problems can be met in other sectors of activity than the field of petroleum, as for example in the field of wastewater treatment, in particular the sewage treatment plants based on the implementation of settlers. It indeed proves extremely important to characterize the fluid entering into a treatment plant so as to be able to propose an optimum solution for this treatment, whatever it is.

Eventually, it exists today no means allowing to characterize correctly the behaviour of a multiphasic fluid so as, for example, to pilot efficiently the operation of a plant for the treatment of a multiphasic fluid.

DISCLOSURE OF THE INVENTION

Consequently, the objects assigned to the present invention aim to remedy the different drawbacks listed above and to propose a new plant for the treatment of a multiphasic fluid, whose operation piloting is optimised and which allows for providing provide, rapidly and without disturbance of the exploitation, useful information for piloting the plant operation.

Another object of the invention aims to propose a new plant for the treatment of a multiphasic fluid, whose operation is particularly reliable, and which allows better separation and production rates.

Another object of the invention aims to propose a new plant for the treatment of a multiphasic fluid that is easily adaptable to any existing production unit.

Another object of the invention aims to propose a new plant for the treatment of a multiphasic fluid of particularly simple and robust conception.

Another object of the invention aims to propose a new method for characterizing a multiphasic fluid allowing to optimise the piloting of the operation of a plant treating such a fluid.

Another object of the invention aims to propose a new method for characterizing a multiphasic fluid allowing to control the separation of such a fluid within a treatment plant.

The objects assigned to the invention are achieved by means of a plant for the treatment of a multiphasic fluid comprising at least two liquid phases of different respective densities, said plant comprising a circuit within which said multiphasic fluid is intended to circulate, said circuit comprising a main settler intended to separate at least said liquid phases, said main settler comprising at least one inlet through which said multiphasic fluid is intended to enter into the main settler and at least one outlet through which said fluid is intended to be discharged from the main settler, said plant being characterized in that it also comprises a tool for characterizing said multiphasic fluid, said characterization tool comprising at least:
  one inlet opening and one outlet opening respectively connected to said circuit upstream of said inlet and upstream of said outlet with respect to the flowing direction of said multiphasic fluid within the circuit,
  an analysis settler arranged between said inlet and outlet openings and adapted to separate at least said liquid phases to obtain so-called separated phases,
  a means for combining said separated phases,
said plant being designed to divert a fraction of the multiphasic fluid circulating in the circuit towards and into the characterization tool, so that the main settler and the characterization tool are concomitantly fed with multiphasic fluid, wherein said fraction of the fluid circulates within the tool entering by said inlet opening to pass through said analysis settler so that said phases are separated then discharged through said outlet opening into said circuit, said combining means being designed to combine said separated phases downstream of said analysis settler and upstream of said outlet with respect to the flowing direction of the fluid.

The objects assigned to the invention are also achieved by means of a method for characterizing a multiphasic fluid comprising at least two liquid phases of different respective densities, said fluid being Intended to circulate within a circuit comprising a main settler intended to separate at least said liquid phases, said main settler comprising at least one inlet through which said multiphasic fluid is intended to enter into the main settler and at least one outlet through which said fluid is intended to be discharged from the main settler, said method being characterized in that it comprises the following steps:
- a step of diverting a fraction of the fluid towards an analysis settler, so that the main settler and the analysis settler are concomitantly fed with multiphasic fluid, said fraction forming an analysis flow passing through said analysis settler, so as to separate at least said liquid phases, and flowing from the latter as separated phases,
- a step of combining said separated phases,
- a step of injecting said separated phases into said circuit upstream of the outlet of the main settler.

BRIEF DESCRIPTION OF THE DRAWINGS

Other objects and advantages of the invention will be better understood from the reading of the following description, as well as thanks to the appended drawings, given only by way of illustrative and non-limitative example, in which.

BEST WAY TO IMPLEMENT THE INVENTION

The present invention relates to a plant 1 for the treatment of a multiphasic fluid comprising at least two phases of different respective densities, and in particular at least two liquid phases of different respective densities, hereinafter called "first phase" and "second phase" respectively. Generally, one of the phases is spread in the other. Within the meaning of the invention, a liquid constitutes a phase when the different elements that compose it cannot be separated by gravity. Hence, a mixture of miscible liquids constitutes a single and same phase.

By way of example, the treatment plant 1 according to the invention can constitute one element of a petroleum production unit. In this situation, the object of the plant 1 according to the invention is to collect the valuable phases (petroleum) of the multiphasic fluid and to discharged towards the outside, or towards other plants, the other phases (water, etc.). By way of alternative, the separation plant 1 may for example constitute one element of a sewage treatment plant. In this case, the multiphasic fluid comprises waters altered by human activities after a domestic, industrial or agricultural use. The first phase is then constituted by water that is desired to be collected, whereas the wastes and/or the pollutants constitute the second phase. For questions of concision and simplicity of description, the following description will be focused on the preferential example of a plant 1 forming one element of a petroleum production site. Of course, the invention is not limited to this preferential application, and any other situation in which it is required to treat a multiphasic fluid comprising liquid phases of different densities enters within the framework of the invention.

In order to collect the valuable phase(s), the plant 1 for the treatment of a multiphasic fluid comprises a main settler 2 intended to separate at least said liquid phases. The main settler 2 is hence a production settler intended to produce industrially a valuable liquid. In the case of the preferential application of the invention, i.e. the petroleum production, the multiphasic fluid entering into the main settler 2 is an emulsion including a liquid organic phase (containing the petroleum that is the valuable phase), forming said first phase, a liquid aqueous phase, forming said second phase, and a gaseous phase. The first function of the main settler 2 is in this case to separate the two liquid phases, the gaseous phase being extracted from the main settler 2, through a vent 22C formed at the apex of the main settler 2 and communicating with a gas treatment plant for valuing or burning these latter. The treatment plant 1 hence constitutes a separation plant allowing to produce a valuable liquid by separation (herein by gravity) of at least two liquid phases of a primary multiphasic fluid.

As illustrated in the Figures, the plant 1 according to the invention comprises a circuit 4 within which the multiphasic fluid is intended to circulate, said circuit 4 comprising in this case said main settler 2. The circuit 4 is consisted of a set of pipes and various devices, within which the fluid circulates. It hence delimitates the path followed by the multiphasic fluid to be transformed. In the preferential example of application of the invention (petroleum production), the circuit 4 extends at least in part between the petroleum deposit and the site of delivery of the petroleum crude. It hence comprises the locations through which said multiphasic fluid flows, and to which belongs in particular the main settler 2 as exposed hereinabove. Preferentially, the circuit 4 comprises at least one multiphasic fluid supply duct 5 allowing in particular the feeding with multiphasic fluid of the main settler 2 to transport, preferentially continuously, a flow of multiphasic fluid towards and into the main settler 2. The supply duct 5 may also be connected to other elements of the plant 1 or of the industrial site to which belongs the plant 1. It may in particular be formed of pipes and junctions within which the multiphasic fluid circulates.

Figure 1:
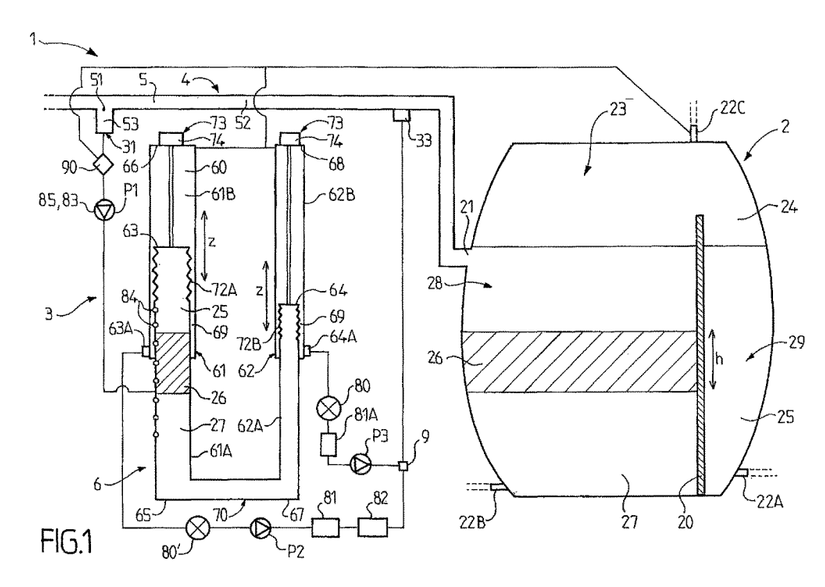
FIG. 1 illustrates, in a sectional schematic view, an example of a plant for the treatment of a multiphasic fluid according to the invention, said plant being in operation and including a main settler and an analysis settler.

An example of a separation plant 1 according to the invention is generally and schematically illustrated in FIG. 1. The separation plant 1 advantageously comprises a main settler 2 intended to separate at least said liquid phases of said multiphasic fluid as described hereinabove. This main settler 2 comprises at least one inlet 21 through which the multiphasic fluid is intended to enter into the main settler 2, to feed the latter. The inlet 21 hence forms the junction interface between the inner volume of the main settler 2 and the outside (i.e. the remaining of the circuit 4). Preferentially, the supply duct 5 is connected to the inlet 21 of the main settler 2, the feeding with fluid being preferentially made in the liquid layer. The main settler 2 also comprises at least one outlet 22A, 22B, 22C through which said fluid is intended to be discharged from the main settler 2, in this case as separated phases. Hence, when the main settler 2 is in operation, the multiphasic fluid circulates continuously therein. Advantageously, the main settler 2 is an industrial settler, i.e. it constitutes a production settler adapted, in terms in particular of capacity and inner arrangements, to treat industrial quantities of multiphasic fluid (petroleum emulsion or wastewater, for example).

Preferably, the main settler 2 is a gravity settler, of the separator tank type. It has the form of a tank (whose envelop is generally metallic) within which circulates continuously the multiphasic fluid the phases of which are desired to be separated. The capacity of the tank and the speed of displacement of the multiphasic fluid are such that the time of residence of the multiphasic fluid (emulsion) within the settler 2 is long enough to allow the liquid phases of different densities to be separated by gravity. The main settler 2 advantageously comprises a separation chamber 23 within which the separation of the different phases of the multiphasic fluid occurs. The gravity is the main physical phenomenon that allows this separation in the following manner: the multiphasic fluid enters into the settler and remains therein during a certain period of time, called time of residence; this time of residence is long enough to allow the different liquid phases to be separated by being vertically distributed as a function of their respective densities. The separated liquid phases are then discharged separately from the main settler 2, through respective outlets 22A, 22B. Within the meaning of the invention, a separated phase can all the same contain residual quantities of another phase of said fluid. Advantageously, the main settler 2 also comprises an inner wall 20, advantageously open at the upper part, allowing to delimitate within the separation chamber 23 two sub-chambers 28, 29 designed to allow the exit of each of the phases to be separated, it being understood that the main settler 2 further comprises for that purpose outlets 22A, 22B, 22C intended to allow the discharge of the separated phase. FIG. 1 illustrates an example of a main settler 2 comprising three outlets: the first outlet 22B is intended to discharge the densest liquid phase (generally the aqueous phase), the second outlet 22A is intended to extract the liquid organic phase (comprising the petroleum), and the third outlet 22C is intended to discharge the gaseous phase. Of course, other types of settlers exist and the invention is not limited to a particular type of settler, whether it includes or not an Inner wall 20.

The separation within a single main settler 2 may prove more or less imperfect. It is hence conceivable, without thereby departing from the framework of the invention, to connect several settlers 2 in series, or more generally in cascade, to obtain in fine a better degree of separation.

Preferentially, the main settler 2 is cylindrical in shape, which allows it in particular to better withstand the high pressure liable to reign therein (the petroleum extraction is generally performed at a pressure comprised between ten and forty bars). The axis of revolution X-X' of the cylinder may be vertical or horizontal, as a function of the type of main settler 2 considered. Advantageously, the main settler 2 is a circular-basis cylinder, the diameter of the generating circle of which is comprised for example between 1 and 4 m, which extends for example over a length comprised between 5 and 30 m. The operation and the different variants of production settlers are perfectly known as such and hence do not need to be described in more detail herein. The plant 1 according to the invention is hence absolutely not limited to a specific type of main settler 2. For example, the main settler 2 according to the invention may be fixed and be only intended to be positioned permanently in an industrial unit.

As an alternative, the main settler 2 may also be mobile so as to be able to be transported, for example to the site of an oil slick and to separate the phases of the emulsion forming this oil slick.

After having entered into the main settler 2, the emulsion remains during a certain time of residence therein. This time of residence will allow the drops of the light phase (generally the organic phase) to go up to the surface and the drops of the denser phase (generally the aqueous phase) to go down to the bottom of the chamber. The more the drops will be fine, the more this process will be slow. Furthermore, the more the coalescence of the drops of a same phase will be rapid, the more the separation process will be short. Within the main settler 2, the multiphasic fluid is dissociated into different sectors whose compositions are clearly different from each other. These sectors are vertically distributed within the main settler 2. The upper sector 24 comprises the gaseous phase, whereas the lower sector comprises the liquid phases. The gaseous phase is discharged from the main settler 2 via a dedicated discharging system 22C, as for example a vent. The lower sector is divided into three superimposed areas. The upper area 25 includes the lighter phase, which corresponds for example to the liquid organic phase (oil). The lower area 27 includes the denser phase, which corresponds for example to the aqueous phase. Between these two areas is generally located an intermediate area 26, forming a layer between said aqueous and organic phases, comprising a mixture of these latter. This layer is in particular called "coalescence layer". The distribution of these different sector 24 and upper 28, intermediate 26 and lower 27 areas is illustrated in particular in the sectional view of the main settler 2 of FIG. 1.

The invention ensues in particular from the observation that the properties of the intermediate area 26 depend on the physico-chemical properties of the entering emulsion. In certain cases, the aspect of the intermediate area can be likened to that of a foam. Now, it has been observed that the drainage of this foam could sometimes be the longer process of the separation. This has shown the interest of focusing in particular on the study of the behaviour of this intermediate area 26 to characterize the separation of the phases of the multiphasic fluid. Advantageously, the study of this area 26 also allows for improvement of the efficiency of the separation within the main settler 2. The height h (thickness) of this area 26 will play a significant role on the performance of the main settler 2. Knowing the properties of this area 26 is from then on important for analysing the operation of the main settler 2.

But a direct study is complex to perform because the measurements inside the main settler 2 are difficult to implement, above all if it is desired to avoid disturbing the production, which is essential. It is hence important to pay interest to the properties of separation of the multiphasic fluid to pilot correctly the operation of the main settler 2. Preferentially, the invention has for object to characterize the gravity separability of the multiphasic fluid circulating within the plant 1. Within the meaning of the Invention, the gravity separability of a multiphasic fluid characterizes the speed at which the different phases constituting the mixture are separated from each other under the effect of gravity. The invention hence consists in searching to characterize the separability of one phase of the emulsion in another one, i.e. the time required for a phase present in the emulsion to be separated from the emulsion. For that purpose, it is not only necessary to pay interest to this coalescence layer, the area 26, but also to know the settleability properties of the drops of one phase in another one, i.e. the propensity of the drops of a phase present in another phase to be separated under the effect of gravity. The characterization of these two phenomena allows the characterization of the gravity separability of the emulsion.

The separation plant 1 according to the invention also comprises a tool 3 for characterizing the multiphasic fluid. This characterization tool 3 has for object to allow the access to parameters determining the behaviour of the multiphasic fluid during the separation of the phases thereof under the effect of gravity. Advantageously, these parameters are liable to reflect and/or to have an influence on the operation and the possible dysfunctions of the main settler 2. The characterization tool 3 is then designed to provide help to the decision taking for piloting the operation of the main settler 2. More generally, it allows characterization of the properties of an emulsion. The characterization tool 3 comprises at least one inlet opening 31, and one outlet opening 33, both connected to said circuit 4. More precisely, the inlet opening 31 and the outlet opening 33 are connected to the circuit 4 upstream of said inlet 21 of the main settler 2 and upstream of said outlets 22A, 22B, 22C of the main settler 2, respectively, with respect to the direction of flowing of said multiphasic fluid within the circuit 4. Within the meaning of the invention, the characterization tool 3 does not itself belong to the circuit 4 and is simply connected to the latter. The characterization tool 3 is hence connected, preferably permanently and continuously, as a diversion of the circuit 4, so that a fraction, preferably a minority, of the flow of multiphasic fluid circulating in the circuit 4 is diverted into the characterization tool 3 before being re-introduced into the circuit 4. This diversion is in this case performed thanks to the fact that the Inlet 31 and outlet 33 openings are both connected to the circuit 4, wherein the outlet opening 33 can be positioned upstream or downstream, but preferentially upstream, of said inlet opening 31, in the direction of flowing of the multiphasic fluid within the circuit 4. This partial diversion of the flow of fluid circulating within the circuit 4 towards the characterization tool 3 ensures that the analysis of the multiphasic fluid within the characterization tool 3 will give results representative in real time of the fluid treated within the plant 1. This diversion also allows the performing of measurements on the entering emulsion within the circuit 4 without disturbing the continuous flowing of the multiphasic fluid within the plant 1. Diverting a minority and preferably insignificant fraction (in terms of quantity) of the flow of the entering emulsion to analyse it hence allows performing rapid, continuous and efficient measurements on the multiphasic fluid. This constitute one of the contributions of the invention. Besides, the characterization tool 3 is designed in such a manner that the fluid having circulated therein is discharged into the circuit 4, into the main settler 2 or upstream thereof, without disturbing the operation of the plant.

As exposed hereinabove, the inlet opening 31 and the outlet opening 33 are connected upstream of said inlet 21 and upstream of said outlet 22A, 22B, 22C, respectively, with respect to the direction of flowing of said multiphasic fluid within the circuit 4, in order to divert, preferably in a permanent and continuous way, a part of the multiphasic fluid circulating in the circuit 4 towards and into the analysis tool 3. Consequently, the multiphasic fluid entering into the characterization tool 3 is hence substantially similar to the multiphasic fluid entering into the main settler 2. The results obtained by the study of the multiphasic fluid circulating within the characterization tool 3 are hence easily transposable for the study of the operation of the main settler 2.

Advantageously, the supply duct 5 is provided with a fork 51 dividing said duct 5 into at least one first branch 52 and one second branch 53. Said first and second branches 52, 53 are advantageously each consisted of one or several pipe(s) allowing the circulation of the multiphasic fluid from the extraction site towards the main settler 2 and the analysis tool 3, respectively. The first branch 52 is preferentially connected to said inlet 21, whereas the second branch 53 is connected to said inlet opening 31 to allow the concomitant feeding with multiphasic fluid of the main settler 2 and the analysis tool 3. The first and second branches 52, 53 may also be subdivided into different branches or connected to other parts of the circuit 4, without thereby departing from the framework of the invention. In other words, the plant 1 is designed to divert a fraction of the multiphasic fluid circulating in the circuit 4 towards and into the characterization tool 3, so that the main settler 2 and the characterization tool 3 are fed concomitantly with multiphasic fluid.

As exposed hereinabove, the outlet opening 33 is connected upstream of said outlets 22A, 22B, 22C in the direction of flowing of the multiphasic fluid within the circuit 4, so as to re-introduce the multiphasic fluid that has passed through the characterization tool 3 into the circuit 4. This avoids the loss of aqueous and organic phases issued from the passage of the multiphasic fluid through the analysis settler 6. Advantageously, the outlet opening 33 is connected to said duct 5 and/or to said main settler 2, so as to re-inject the fluid diverted from the circuit 4 into the circuit 4, either directly into the main settler 2, or upstream of the main settler 2, so that at least one fraction of the thus re-injected fluid is treated by the main settler 2. The injection may be performed in any place upstream of the outlet of the main settler 2, so that the different phases of the fluid having circulated within the characterization tool 3 can be subsequently separated by the main settler 2.

Advantageously, the gaseous phase present within the emulsion is at least partially pre-separated in the characterization tool 3, before the multiphasic fluid enters into the analysis settler 6. This pre-separated gaseous phase is then re-injected into the circuit 4, preferentially towards the outlet 22C, intended to discharge the gas from the main settler 2. Preferentially, this operation is performed by means of a pre-separator 90 located at or upstream of the inlet opening 31. As an alternative, this pre-separated gaseous phase can also be discharged through a specific outlet that belongs to the circuit 4 within the meaning of the invention. Advantageously, the separation tool 3 also comprises one or several outlets connected to said specific outlet and that allows discharging the gaseous phase.

The characterization tool 3 according to the invention moreover comprises on the one hand an analysis settler 6, arranged between said inlet 31 and outlet 33 openings, and adapted to separate said liquid phases to obtain so-called separated phases, and on the other hand a means 9 for combining said separated phases. The plant 1 is designed so that said fraction of fluid circulating within the tool 3 penetrates through said inlet opening 31 to pass through said analysis settler 6 so that said phases are separated and discharged through said outlet opening 33 in said circuit 4, said combination means 9 being designed to combine said separated phases downstream of the analysis settler 6 and upstream of said outlets 22A, 22B, 22C of the main settler 2 with respect to the flowing direction of the fluid. The combination means 9 allows for remixing the phases within the multiphasic fluid. Hence, the analysis settler 6, although it separates the phases, has no impact on the composition of the multiphasic fluid circulating within the circuit 4. This combining means 9 is advantageously formed by a connection, located upstream of the outlet opening 33, of the ducts supplying the different phases coming from the analysis settler 6. In this situation, the phases are injected into the circuit 4 after being already combined. As an alternative, the phases can be discharged in different locations of the circuit 4. In such a case, the combining means 9 is formed by the duct of the circuit 4 where the phases are combined together. The separated phases are mixed together within the multiphasic fluid and are not injected into the circuit 4 in a combined state but in a separated state. Hence, the characterization tool 3 has no direct impact on the operation of the plant 1, it serves only to provide information about the multiphasic fluid circulating therein. This information can then be useful to improve the operation of the plant 1.

Advantageously, the characterization tool 3 comprises a means 83 for limiting the flow rate of multiphasic fluid entering into said tool 3, so that the flow rate of multiphasic fluid entering into said characterization tool 3 is lower than the flow rate of the multiphasic fluid circulating in said circuit 4 at said inlet opening 31. In practice, the introduction of the multiphasic fluid Into the analysis settler 6 is preferably performed by means of a pump P1, preferably a positive displacement pump, such that the flow rate of supply of the analysis tool can be easily adjusted by variation of the rotation speed of the pump 83. Hence, the flow rate of the flow of multiphasic fluid circulating within the characterization tool 3 is preferably far lower than that circulating within the circuit 4 at the inlet opening 31, and so that advantageously the times of residence in the characterization tool 3 and in the main settler 2 are comparable. The fact to divert a restricted part of the total flow of the entering multiphasic fluid allows to easily make the measurements required for the analysis of this fluid without risking to compromise the transformations operated within the treatment plant 1.

Preferentially, this limitation means 83 allows for reducing the flow rate by a factor of 10, or more preferentially, a factor of 100, or even 100000, with respect to the flow rate circulating within the circuit 4, at the inlet opening 31.

Preferentially, the discharge of the multiphasic fluid from the analysis settler 6 is performed by means of pumps P2, P3, whose flow rate is adjusted so as to stabilise the volumes of the separated phases contained in the analysis settler 6, and in particular to control them by adjusting the speeds of rotation of said pumps P2, P3.

Advantageously, the analysis settler 6 operates in parallel with the main settler 2. Hence, the fluid circulates note only within the main settler 2, but also within the characterization tool 3, by entering through said Inlet opening 31, passing through said analysis settler 6 and being discharged through said outlet opening 33 towards the circuit 4. Hence, the characterization tool 3 evaluates the properties of the multiphasic fluid when the latter circulates therein.

Preferentially, the fluid hence advantageously circulates continuously both within the main settler 2 and within the analysis settler 6, as two parallel flows, i.e. a production flow (majority) and an analysis flow (minority). One of the functions of the analysis settler 6 is to be able to separate the phases of the multiphasic fluid in parallel with the main settler 2 in order, in particular, to be able to easily perform physico-chemical measurements on theses thus-separated phases. This allows access in continuous and in real time to the various properties of these phases.

The analysis settler 6 advantageously allows simulation at least in part and in real time the operation of the main settler 2. The analysis settler 6 hence allows acceding to different parameters relative to a flow of fluid similar to that entering Into the main settler 2, because diverted from the flow of fluid feeding the main settler 2, and this without disturbing the operation of the main settler 2. The analysis settler 6 is preferably designed to offer settlement conditions similar or close to those of the main settler 2, to within a possible scale effect, without this implies that way an absolute mimicry, the essential being that the settlement conditions are close enough so that the separation occurring within the analysis settler 6 provides pertinent information to characterize the emulsion as well as to analyse the operation of the main settler 2.

The analysis settler 6 advantageously comprises a separation chamber 60 within which the multiphasic fluid is intended to circulate so that the phases thereof are separated under the effect of gravity. Advantageously, the volume of the separation chamber 23 of the main settler 2 is at least ten times greater than the volume of the separation chamber 60 of the analysis settler 6, preferentially at least one hundred times greater.

Advantageously, the analysis settler 6 operates according to the principle of the Florentine well and preferably constitutes such a Florentine well.

Figure 2:
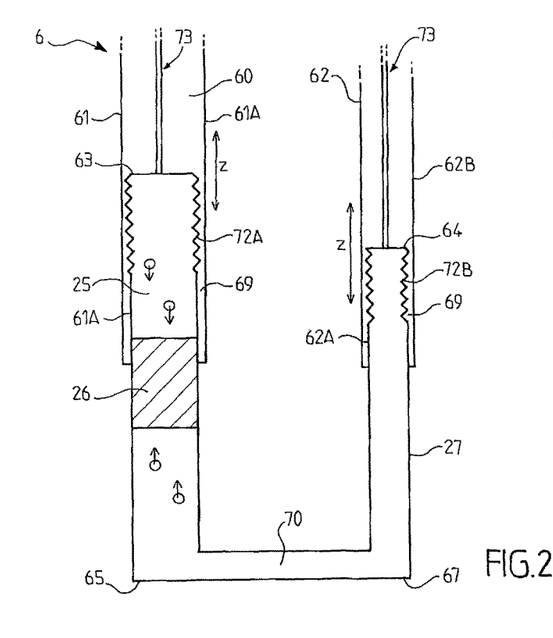
FIG. 2 shows, in a sectional schematic view, an analysis settler of the plant of FIG. 1, said analysis settler being in operation.

Preferentially, said analysis settler 6 comprises at least on the one hand a separation channel 61 provided with a first outlet orifice 63 and extending vertically between a first base 65 and a first apex 66 and on the other hand a flowing channel 62 provided with a second outlet orifice 64 and extending vertically between a second base 67 and a second apex 68. The first separation channel 61 is connected to the inlet opening 31 to feed the analysis settler 6 with fluid. The separation into different phases of the multiphasic fluid is performed within the separation channel 61, whereas the flowing channel 62 is intended for the discharge of one of said phases (the dense phase). The separation 61 and flowing 62 channels can be of any shape, for example cylindrical or parallel piped, the importance being that they have a certain vertical extension (height) to allow the settlement of the fluid therein.

The outlet orifices 63, 64 constitute the locations through which the multiphasic fluid is discharged from the analysis settler 6. Preferentially, the discharge is performed by pouring of the fluid at the outlet orifices 63, 64. These outlet orifices 63, 64 are preferentially connected to the outlet opening 33. They can be formed for example as a hole, advantageously of large enough size to allow a free flowing by pouring, arranged within each separation 61 and flowing 62 channels.

Preferentially, the separation 61 and flowing 62 channels are formed of telescopic tubes 61A, 61B, 62A, 62B sealingly connected to each other. The tubes of larger diameter 61B, 62B cover at least in part the tubes of smaller diameter 61A, 62A. An interstice 69 is hence formed by the walls of the tubes of smaller diameter 61A, 62A and of the tubes of larger diameter 61B, 62B at this overlap. The tubes of smaller diameter 61A, 62A form the lower part of the separation 61 and flowing 62 channels and the multiphasic fluid circulates therein. The outlet orifices 63, 64 are from then on formed by the terminal orifices of the tubes of lower diameter 61A, 62A, respectively, and hence form weirs. The fluid can then overflow from the tubes of lower diameter 61A, 62A through the outlet orifices 63, 64 to circulate in the interstice 69, between the tubes of lower diameter 61A, 62A and of larger diameter 61B, 62B, up to a connection 63A, 64A connected to said outlet opening 33 through pumps P2 and P3. In this case, the respective altitude of the outlet orifices 63, 64 within each separation 61 and flowing 62 channel defines the maximum height that can be reached by the fluid within each separation 61 and flowing 62 channel. Such a solution has advantages when the positions of the outlet orifices 63, 64 are mobile, such solutions being presented hereinafter.

The analysis settler 6 also comprises a coupling connection 70 sealingly connecting said first and second separation channels 61, 62 at the bases 65, 67 thereof. This connection 70 defines a volume common to the two separation channels. The multiphasic fluid can then circulate within this common volume and in particular pass from one separation to one another. Preferentially, only the denser phase circulates within this coupling 70, the separation being performed at the level of the separation channel 61.

Preferentially, the analysis settler 6 is formed of two separation 61 and flowing 62 channels that are columns connected to each other to form a "U". The columns are advantageously vertical cylinders of the same height. Their diameter may be different. FIG. 2 shows in particular the case where the diameter of the separation channel 61 is larger than the diameter of the flowing channel 62. The arms of the "U" correspond to the separation 61 and flowing 62 channels whereas the horizontal bar of the "U" corresponds to the coupling connection 70.

Preferentially, the separation 61 and flowing 62 channels have a height comparable to that of the main settler 2. Indeed, it may be advantageous that the analysis settler 6 has a behaviour, at the level of the separation, similar to that of the main settler 2. Similar vertical sizes allow to have coalescence conditions that are relatively close, or at least representative, of those within the main settler 2. Preferentially, the pressures and temperatures within the two settlers 2, 6 are also substantially similar. For that purpose, the characterization tool 3 is in particular thermally insulated by means of any known Insulation means.

The outlet orifices 63, 64 are advantageously vertically distributed so as to separate said phases of the fluid. This distribution further ensures the simultaneous presence of layers 27, 28 and possibly 26 within the separation channel 61, according to the known principle of a Florentine well. The altitudes of the outlet orifices 63, 64 are hence different, the altitude of the first outlet orifice 63, through which is discharged the less dense phase (first phase) being higher than that of the second outlet orifice 64, through which is discharged the denser phase (second phase). The altitude of the different outlet orifices 63, 64 determines the altitude of the intermediate area 26 between the two liquid phases of the fluid of different densities. Indeed, the pressures inside the separation 61 and flowing 62 channels at each base 65, 67 of the separation 61 and flowing 62 channels are similar because said bases 65, 67 communicate with each other. To respect this pressure continuity, the different phases of the fluid will be superimposed in a particular way and hence position the intermediate area 26 between the different phases.

The position of the intermediate area 26 depends only on the density of the different phases and of the height of fluid within the separation 61 and flowing 62 channels. It is hence necessary to correctly position the outlet orifices 63, 64 to ensure that this area 26 can well be positioned inside the separation channel 61, that in which the multiphasic fluid enters in first, and hence avoid any major dysfunction. Indeed, if the intermediate area 26 is not positioned in the separation channel 61 (positioned at a too low altitude), then a mixture of phases is liable to enter into the flowing channel 62: from then on, it is no longer possible to collect a pure enough aqueous phase and the analysis settler 6 does then not operate correctly. The possibility to modify the positioning of the orifices 63 and 64 allows the plant to characterize the separability of the multiphasic fluid without a major dysfunction occurs within the analysis settler 6. But such a dysfunction can also be simulated in order to characterize the behaviour of the multiphasic fluid in this type of situation that may occur within the main settler 2, or in order to characterize the thickness of the coalescence layer 26. There could be a reverse dysfunction if the intermediate area were positioned at a too high altitude.

Preferentially, the positioning of the outlet orifices 63, 64 must take into account the geometric specificities of the main settler 2, to provide the multiphasic fluid entering into the analysis settler 6 with conditions of separation that are similar or close to those met in the main settler 2. This positioning must also take into account the respective density of each of the two separated liquid phases. The main settler 2 is sized as a function of the entering emulsion and the analysis settler 6 can undergo the same type of size constraint, in particular for the respective diameters of the separation 61 and flowing 62 channels.

However, the characterization tool 3 may also operate according to a far greater operating range in order not to characterize the settler 2 but the multiphasic fluid that flows through it.

Advantageously, the characterization tool 3 comprises a means for adjusting the vertical position of the first and/or second outlet orifice 63, 64. Thanks to this functionality, the characterization tool 3 is adaptable to any treatment plant 1 or any main settler 2 and to a wide range of emulsions as regards the difference of density. For that purpose, it is just needed to modify the position of the different outlet orifices 63, 64. A single and same characterization tool 3 provided with such an adjustment means can from then on be implemented on different treatment plants 1.

Preferentially, the separation channel 61 and/or the flowing channel 62 comprises (comprise) a deformation portion 72A, 72B. This deformable portion can for example take the form of a bellows whose vertical extension z (i.e. the height) is modifiable. The adjustment means advantageously comprises said deformable portion 72A, 72B, as well as a control member 73 that allows the control of the deformation of said deformable portion 72A, 72B to modify the altitude of said first and/or said second orifice 63, 64, integral with the deformable portion 72A, 728. The control member 73 may for example include a mechanical actuator, such as a cylinder 74 designed to deform the deformable portion 72A, 72B, for example by applying thereto an effort of traction or compression to increase or reduce the height z. The control member 73 advantageously comprises a means for controlling by computer or electronically said actuator, which allows a fine and easy adjustment of the position of the outlet orifice 63, 64 it controls.

Advantageously, the deformable portion is the upper part of the tube of lower diameter 61A, 62A. Hence, the modification of the height z of the outlet orifices 63, 64 does not modify the fluid discharging system. The separation 61 and flowing 62 channels comprise an outlet connection 63A, 64A, respectively, each connected to the outlet opening 33. Hence, the outlet connections 63A, 64A are fixed when the outlet orifices 63, 64 change of altitude.

Besides, the characterization tool 3 advantageously comprises a means 85 for adjusting the flow rate of multiphasic fluid entering into the characterization tool 3. This adjustment means 85 hence allows modifying the time of residence of the emulsion within the analysis settler 6. Advantageously, the means 85 for adjusting the flow rate entering into the analysis settler 6 comprises at least one positive displacement pump P1 mounted upstream of the analysis settler 6 and downstream of the Inlet opening 31. By adjusting the flow rate, it is hence possible to modify the time of residence of the emulsion within the analysis settler 6 and hence to characterize the behaviour thereof as a function of this time of residence. Advantageously, thanks to the adjustment means 85, it is possible for example to adjust the flow rate so that the times of residence of the emulsion within the main 2 and analysis 6 settlers are identical, so that the study of the separation within the analysis settler 6 provides information directly exploitable for piloting the main settler 2, without having to intervene directly on the latter, which would be in practice very complex to implement.

Advantageously, the means 85 for adjusting the entering flow rate also allows cutting the feeding with fluid of the characterization tool 3. This may be interesting if the operator of the plant 1 wants to study the separation of the multiphasic fluid circulating within the circuit 4 only in certain time slots, separated by pause intervals.

Preferentially, the adjustment means 85 can allow not only to impose similar conditions of separation between the main settler 2 and the analysis settler 6, but also to simulate the operation of the main settler 2 in a different operation range, which allows testing solutions intended to optimise the piloting of the operation of the main settler 2. The characterization tool 3 according to the invention is not only useful as a simulator of operation of the main settler 2, but also as a tool for predicting the operation of the main settler 2 with different input parameters. It is hence possible to modify the entering flow rate so as to observe the consequences on the separation of the fluid. If the separation is estimated satisfactory, it will then be possible to apply such a solution for the main settler 2. But the direct application of the solution may also take into account other parameters, as for example the differences between the emulsion circulating within the circuit 4 and that circulating within the analysis settler 6. These differences may in particular come from the fragmentation of the drops during the diversion of the fraction of multiphasic fluid flow circulating within the circuit 4. It is hence possible to optimise the operating conditions as a function of the real behaviour of the emulsion and the specifications of the separated phases.

Advantageously, the characterization tool 3 comprises an additional inlet allowing the addition of chemical additives within the characterization tool 3, preferably upstream of or directly into the analysis settler 6. Hence, the characterization tool 3 advantageously allows simulating the addition of additives into the main settler 2. It is hence possible, by means of the characterization tool 3 according to the invention, to play in real conditions on the two main levers (flow rate, nature and content of the chemical additives) allowing to pilot the main settler 2, without thereby intervening on the main settler 2 itself. The characterization tool 3 hence allows determining the optimum adjustment for the main settler 2, without risking to disturb the production.

Preferentially, the characterization tool 3 comprises a means for locating, within said analysis settler 6, phases of said multiphasic fluid and hence the intermediate area 26, in order in particular to know the height h of this intermediate area 26. The location means in question allows in particular to know if this area 26 is effectively located within the first separation channel 61 and not at least in part in the second separation channel, which would be synonymous with a dysfunction of the analysis settler 6. The measurement of the height h of the intermediate area 26 can be performed continuously, which ensures that it does not increase or does not risk to go into the flowing channel 62. By studying this area 26, particularly pertinent information for the characterization of the separability of the fluid can be collected, in particular by collection of information about the coalescence phenomenon occurring within this area 26. This also allows predicting possible future dysfunctions of the main settler 2.

Said locating means is for example formed by several pressure sensors 84 vertically distributed within the separation channel 61. Indeed, the composition and/or the physicochemical properties of the fluid, in particular the density thereof, have an influence on the pressure induced by the column of liquid so that a series of measurements of pressure performed along the channel 61 allows locating the different phases, the cartography of the pressures allowing to deduce the cartography of the phases. According to another variant, said location means may be formed by fl radiation absorption probes vertically distributed, which give a direct measurement of the density of the fluid in contact with them. This phase cartography can from then on be easily obtained.

Hence, as exposed hereinabove, the analysis settler 6 allows the separation of the multiphasic fluid, as illustrated in particular thanks to FIG. 2. This figure shows only the analysis settler 6, without the remaining of the separation plant 1. The two phases are discharged by overflowing at the two outlet orifices 63, 64. Hence, the carrier fluid (that which constitutes in majority the emulsion) circulates within the separation channel 61 with a certain vertical speed, which is not null but low enough to allow the separation of the phases. If the settlement speed of a drop on one of the phases is lower than the speed of the carrier fluid, this drop won't be able to reach the outlet orifice 63, 64 through which the corresponding phase is discharged. This situation is shown in FIG. 2 with the presence of drops of one phase in another one at the two outlet orifices 63, 64. The drops of small size are of course more difficult to separate because their settlement speed is low. The analysis of the different oil and waters exits over time hence allows measuring the performance of separation of the analysis settler 6 and indirectly those of the main settler 2, or in an absolute way to characterize the gravity separability of the emulsion.

Different measurements are advantageously performed at one and/or the other outlet 63, 64 through which the different phases are respectively discharged. Preferentially, these measurements are performed at the two outlets. For that purpose, the characterization tool 3 comprises for example at least one apparatus 80 measuring the flow rate of one of said phases separated and discharged through one of said outlet orifices 63, 64. As a first approach, the flow rate through an outlet corresponding to a phase is substantially equal to the total flow rate multiplied by the proportion of this phase within the multiphasic fluid. Hence, the measurement of the flow rate of a given phase allows acceding to the proportion of one phase in another one. This measurement that is relatively simple to implement allows to rapidly and directly collect Information of the composition of the entering emulsion, such information being of course important for the operator of a petroleum production site.

Such a measurement apparatus 80 is advantageously positioned downstream of the separation 61 and flowing 62 channels and upstream of the outlet opening 33. It can measure the flow rate of the aqueous phase, whereas another apparatus 80' can possibly measure the flow rate of the organic phase.

Preferentially, the characterization tool 3 comprises at least one sensor 81 measuring the density of one of said phases separated and discharged through one of said outlet orifices 63, 64, said sensor 81 being arranged between said one of said outlet orifices 63, 64 and said outlet opening 33. This type of measurement allows to have information about the fluid circulating through this outlet orifice 63, 64, and hence prevents very rapidly any dysfunction of the main settler 2. Preferably, the characterization tool 3 comprises two sensors 81, 81A positioned downstream of said first and second outlet orifices 63, 64 and upstream of the outlet opening 33, respectively, so as to take measurements on one and/or the other of the phases separated by the analysis settler 6.

Advantageously, the characterization tool 3 further comprises at least one apparatus 82 measuring, in one of said phases separated and discharged through one of said outlet orifices 63, 64, the possibly present residual quantity of another phase of said multiphasic fluid. This type of measurement allows evaluation of the performance of the analysis settler 6 at a given flow rate. The separability of the fluid at a given flow rate is hence measured. This series of measurements is then used to apply the more successful solution (variation of flow rate or addition of chemical additives) to the main settler 2.

The measurements presented above are implemented substantially more easily within the analysis tool 6 rather than at the outlets 22A, 22B of the mail settler 2. Indeed, it may be particularly advantageous, in order to characterize finely and "in situ" the behaviour of the multiphasic fluid, to vary the flow rate of said fluid, in particular to determine its intrinsic "separability". Now, it is not conceivable to vary the flow rate of production of the main circuit to perform these measurements, because it would unacceptably disturb the production. It is hence not possible to predict the behaviour of the multiphasic fluid by means of measurements on the outlets 22A and 22B. Offsetting by diversion the location of measurement, according to the invention, ensures a better accuracy because the environment of the characterization tool 3 has been precisely designed to optimize this measurement taking.

Hereinabove, we have described an analysis settler 6 able to separate two liquid phases and a gaseous one. The characterization tool 3 according to the invention also allows analyzing the separation of a triphasic liquid or comprising far more distinct phases. A variant of an analysis settler 6 of the invention intended to separate three liquid phases Is shown in FIG. 3.

Figure 3:
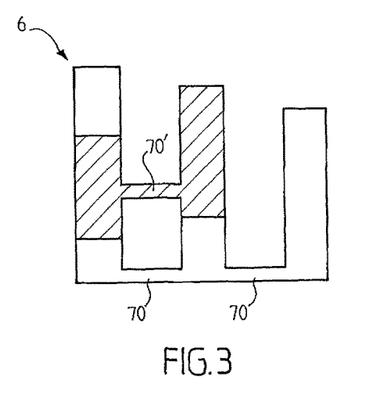
FIG. 3 illustrates, in a sectional schematic view, a second example of an analysis settler belonging to a plant according to the invention designed to separate three liquid phases of a multiphasic fluid, said analysis settler being in operation.

In an embodiment of FIG. 3, the analysis settler 6 comprises three separation channels, each of which is provided with an outlet intended to discharge a separate phase. These separation channels extend vertically between bases and apexes. All the bases of these channels are connected together by a coupling connection 70. Moreover, the two first channels are also connected by an additional coupling connection 70', arranged at a higher altitude than that of the coupling connection 70, so as to allow the phases of the fluid to be distributed within the different separation channels. The differences of density between the phases of the multiphasic fluid impose the altitude of this additional coupling 70'. Advantageously, the altitude of the coupling 70' may be modified so that this variant can be easily adapted to a wide range of fluids. The general operation is similar to that of a characterization tool 3 intended for the separation of a biphasic liquid as described hereinabove. As an alternative, it is also possible de connect two characterization tools 3 in series. In this situation, the multiphasic fluid enters into the inlet opening 31 of the first characterization tool 3, the first phase being separated and discharged through the first outlet orifice 63, the two other phases being discharged through the second outlet orifice 64. It is from then on just needed to connect this outlet orifice 64 to the inlet opening 31 of the second tool 3 to allow the separation of the two other phases.

The invention also relates to a method for characterizing a multiphasic fluid comprising at least two liquid phases of different respective densities, said method being advantageously intended to be implemented by means of the plant 1 according to the above description. All the description relating to the plant 1 and the operation thereof is hence also true for the present method. As exposed hereinabove, said fluid is intended to circulate within a circuit 4 comprising a main settler 2 intended to separate at least said liquid phases, said main settler 2 comprising at least one inlet 21 through which said multiphasic fluid is intended to enter into the main settler 2 and at least one outlet 22A, 22B, 22C through which said fluid is intended to be discharged from the main settler 2. The physico-chemical characteristics of the multiphasic fluid depend in particular on the upstream conditions of production of the multiphasic fluid. Advantageously, the fluid enters into the main settler 2 as an entering flow.

The method according to the invention comprises, as exposed hereinabove, a step of diverting a fraction of the fluid towards an analysis settler 6, so that the main settler 2 and the analysis settler 6 are fed concomitantly with multiphasic fluid, said fraction forming an analysis flow passing through said analysis settler 6, so as to separate at least said liquid phases, and going out of the latter as separated phases. The separated phases advantageously form an analysed flow. Hence, the analysed flow represent a portion of the flow of fluid circulating within the circuit 4 at the level of the diversion. Advantageously, the location of the diversion is located upstream of said inlet 21 of said main settler 2.

The analysed flow is, within the meaning of the invention, the flow of fluid at the outlet of the analysis settler 6. Advantageously, the analysis settler 6 allows the separation of said phases of the fluid and comprises at least a first and a second outlet orifices 63, 64 through which said separated phases are respectively discharged. Hence, the analysed flow is advantageously formed of two separated sub-flows of different phases.

Preferentially, the method according to the invention comprises a step of adjusting the flow rate of said analysis flow circulating through said analysis settler 6 by modifying the quantity of fluid forming said fraction. Preferably, this adjustment step comprises a step of increasing or reducing the flow rate. This allows in particular to modify the time of residence of the fluid within the analysis settler 6. Advantageously, the method according to the invention also comprises a step of introducing chemical additives into the main settler 2.

The method according to the invention also comprises, as exposed hereinabove in relation with the description of the separation plant 1, a step of injecting said separated phases into said circuit 4, upstream of the outlet 22 of the main settler 2. The plant 1 according to the invention characterizes the multiphasic fluid circulating therein, which requires the separation of said phases. But this separation has no consequences on the production because the separated phases are both re-injected into the circuit 4. Advantageously, the fluid circulate continuously and simultaneously within both the analysis settler 6 and the main settler 2.

The method according to the invention also comprises a step of combing said separated phases. The combination of these separated phases is performed preferably downstream of the analysis settler 6 with respect to the direction of flowing of said fraction within said tool 3. As exposed hereinabove, this combination may occur upstream of the outlet opening 33 or directly within the circuit 4 if the separated phases are directly injected into the circuit 4. Hence, the combination step may occur before or after the step of injection.

Preferentially, the method of analysis according to the invention comprises a step of measuring the density of one of said separated phases allowing in particular to ensure any major dysfunction of the analysis settler 6.

Advantageously, the method of analysis according to the invention comprises a step of measuring, in at least one of said separated phases, the possibly present residual quantity of another phase of said fluid. This measurement can be performed by any known means, as for example by means of a capacitive or optical sensors. This information proves useful to accede to the separation performance of the analysis settler 6 and hence also by deduction of that of the main settler 2.

Preferentially, the method of analysis according to the invention comprises a step of measuring the flow rate of one of said separated phases. As explained hereinabove, this allows in particular to know the respective proportions of the phases within the multiphasic fluid.

Advantageously, the method of the Invention allows, from the steps described hereinabove, to characterize the separability of the multiphasic fluid circulating within the circuit 4. For that purpose, the method advantageously comprises the following successive steps:

- a step of adjusting the analysis flow at a first measurement flow rate. The measurement flow rate may then take arbitrarily high or low values.
- a step of measuring in one of said separated phases the possibly present residual quantity of another phase of said fluid, allowing the determination of a measurement value corresponding to said first measurement flow rate. Advantageously, this measurement of residual content is performed on the two outlets 63, 64 of the analysis settler 6 so as to have a particularly accurate measurement.
- a step of storing said measurement value as a function of said measurement flow rate. The measured values are hence stored so as to be able to be easily transmitted and analysed.

The flow adjustment, measurement and storage steps are repeated at different flow rates so as to characterize the separation of said fluid as a function of the measurement flow rate. Advantageously, a curve of the residual content of one phase in another one as a function of the entering flow rate or of the time of residence of the emulsion within the analysis settler 6 can be constructed, the time of residence and the flow rate being proportional to each other. A particularly pertinent information to characterize the emulsion is hence obtained. Preferentially, this information is useful to pilot the operation of the main settler 2 at a maximum flow rate for a residual content of one phase in another one, which is considered as acceptable.

Preferentially, the method of analysis according to the invention comprises a step of locating, within said analysis settler 6, phases of said multiphasic fluid. This may be performed by means of pressure sensors 84. This step of location advantageously comprises the following sub-steps:

- a sub-step of measurement of pressure. This sub-step may for example be performed by means of a series of pressure sensor 84 vertically distributed, so as to cartography the pressure field along a vertical direction. It may also be performed by means of ☐ radiation absorption probes, as exposed hereinabove.
- a sub-step of identification of the vertical extent of the different phases of the fluid, by determination of the abrupt variations of the pressure field, so as to determine the altitude of the different areas 27, 25, 26 mentioned above.

The step of location advantageously comprises a sub-step of measurement of the height h of the intermediate area 26.

The invention claimed is:

1. A plant (1) for the treatment of a multiphasic fluid comprising at least two liquid phases of different respective densities, said plant (1) comprising:
    a circuit (4) within which said multiphasic fluid is configured to circulate, said circuit (4) comprising a main settler (2) configured to separate said at least two liquid phases of different respective densities, said main settler (2) comprising at least one inlet (21) through which said multiphasic fluid is configured to enter into the main settler (2) and at least one outlet (22A, 22B, 22C) through which said fluid is configured to be discharged from the main settler (2), said plant being characterized in that it also comprises a tool (3) for the characterization of said multiphasic fluid, said characterization tool (3) comprising at least:
    one inlet opening (31) and one outlet opening (33) respectively connected to said circuit (4) upstream of said inlet (21) and upstream of said outlet (22A, 22B, 22C) with respect to a flowing direction of said multiphasic fluid within the circuit (4);
    an analysis settler (6) arranged between said inlet (31) and outlet (33) openings and adapted to separate said at least two liquid phases to obtain separated phases, said analysis settler (6) comprising at least one separation channel (61) provided with a first outlet orifice (63) and extending vertically between a first base (65) and a first apex (66) and a flowing channel (62) provided with a second outlet orifice (64) and extending vertically between a second base (67) and a second apex (68), said analysis settler (6) comprising a coupling connection (70) connecting said first and second separation (61) and flowing (62) channels proximate their bases (65, 67), said outlet orifices (63, 64) being connected to said outlet opening (33), said separation channel (61) being connected to said inlet opening (31) to feed said analysis settler (6) with multiphasic fluid, said outlet orifices (63, 64) being vertically distributed so as to separate said at least two liquid phases of the multiphasic fluid, each said separated phase being then discharged through one of said outlet orifices (63, 64); and
    means (9) for combining said separated phases, said plant (1) being designed to divert a fraction of the multiphasic fluid circulating in the circuit (4) towards and into the characterization tool (3), so that the main settler (2) and the characterization tool (3) are concomitantly fed with multiphasic fluid, wherein said fraction of the fluid circulates within the tool (3) entering through said inlet opening (31) to pass through said analysis settler (6) so that said phases are separated then discharged through said outlet opening (33) into said circuit (4), said combining means (9) being designed to combine said separated phases downstream of said analysis settler (6) and upstream of said outlet (22A, 22B, 22C) with respect to the flowing direction of the multiphasic fluid circulating in the circuit (4).

2. The plant (1) for the treatment of a multiphasic fluid according to claim 1, characterized in that said tool comprises a means for adjusting the vertical position of the first and/or second outlet orifice (63, 64).

3. The plant (1) for the treatment of a multiphasic fluid according to claim 2, characterized in that said separation channel (61) and/or said flowing channel (62) comprises (comprise) a deformable portion (72A, 72B) and in that said adjustment means comprises said deformable portion (72A, 72B) as well as a control member (73) allowing to control the deformation of said deformable portion (72A, 72B) to modify the altitude of said first and/or said second orifice (63, 64).

4. The plant (1) for the treatment of a multiphasic fluid according to claim 1, characterized in that said tool (3) comprises at least one apparatus (80) measuring the flow rate of one of said phases separated and discharged through one of said outlet orifice (63, 64).

5. The plant (1) for the treatment of a multiphasic fluid according to claim 1, characterized in that said tool comprises at least one apparatus (82) measuring, in one of said at least two liquid phases of the multiphasic fluid separated and discharged through one of said outlet orifices (63, 64), a present residual quantity of another phase of said multiphasic fluid.

6. A plant (1) for the treatment of a multiphasic fluid comprising at least two liquid phases of different respective densities, said plant (1) comprising:
   a circuit (4) within which said multiphasic fluid is configured to circulate, said circuit (4) comprising a main settler (2) configured to separate said at least two liquid phases of different respective densities, said main settler (2) comprising at least one inlet (21) through which said multiphasic fluid is configured to enter into the main settler (2) and at least one outlet (22A, 22B, 22C) through which said fluid is configured to be discharged from the main settler (2), said plant being characterized in that it also comprises a tool (3) for the characterization of said multiphasic fluid, said characterization tool (3) comprising at least:
   one inlet opening (31) and one outlet opening (33) respectively connected to said circuit (4) upstream of said inlet (21) and upstream of said outlet (22A, 22B, 22C) with respect to a flowing direction of said multiphasic fluid within the circuit (4);
   an analysis settler (6) arranged between said inlet (31) and outlet (33) openings and adapted to separate said at least two liquid phases to obtain separated phases;
   means for locating within said analysis settler (6) phases of said multiphasic fluid; and
   means (9) for combining said separated phases, said plant (1) being designed to divert a fraction of the multiphasic fluid circulating in the circuit (4) towards and into the characterization tool (3), so that the main settler (2) and the characterization tool (3) are concomitantly fed with multiphasic fluid, wherein said fraction of the fluid circulates within the tool (3) entering through said inlet opening (31) to pass through said analysis settler (6) so that said phases are separated then discharged through said outlet opening (33) into said circuit (4), said combining means (9) being designed to combine said separated phases downstream of said analysis settler (6) and upstream of said outlet (22A, 22B, 22C) with respect to the flowing direction of the multiphasic fluid circulating in the circuit (4).

7. The plant (1) for the treatment of a multiphasic fluid according to claim 6, characterized in that said main settler (2) and said analysis settler (6) each comprise a first and a second separation chamber (23, 60), respectively, within which said multiphasic fluid is intended to circulate, a volume of said first separation chamber (23) being at least ten times greater than a volume of said second separation chamber (60).

8. The plant (1) for the treatment of a multiphasic fluid according to claim 6, characterized in that said circuit (4) comprises at least one fluid supplying duct (5) provided with a fork (51) dividing said duct into at least one first and one second branches (52, 53), said first branch (52) being connected to said inlet (21) and said second branch (53) being connected to said inlet opening (31) to allow the concomitant fluid supply of said main settler (2) and said tool (3).

9. The plant (1) for the treatment of a multiphasic fluid according to claim 8, characterized in that said outlet opening (33) is connected to said duct (5) and/or said main settler (2).

* * * * *